(12) United States Patent
Ishida et al.

(10) Patent No.: US 8,324,456 B2
(45) Date of Patent: Dec. 4, 2012

(54) METHOD FOR IMPROVING TRANSFORMATION EFFICIENCY USING POWDER

(75) Inventors: Yuji Ishida, Iwata (JP); Yukoh Hiei, Iwata (JP); Jun Ueki, Iwata (JP); Takeshi Yamamoto, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 784 days.

(21) Appl. No.: 12/086,426

(22) PCT Filed: Dec. 13, 2006

(86) PCT No.: PCT/JP2006/324839
§ 371 (c)(1),
(2), (4) Date: Apr. 20, 2009

(87) PCT Pub. No.: WO2007/069643
PCT Pub. Date: Jun. 21, 2007

(65) Prior Publication Data
US 2011/0131685 A1    Jun. 2, 2011

(30) Foreign Application Priority Data
Dec. 13, 2005    (WO) .................. PCT/JP2005/022863

(51) Int. Cl.
*C12N 15/84* (2006.01)
*A01H 4/00* (2006.01)

(52) U.S. Cl. ..................... 800/294; 800/320; 800/320.1; 800/320.2; 435/430.1; 435/424; 435/469

(58) Field of Classification Search .................. None
See application file for complete search history.

(56) References Cited

U.S. PATENT DOCUMENTS

| | | | |
|---|---|---|---|
| 5,591,616 A | 1/1997 | Hiei et al. | |
| 6,350,611 B1 | 2/2002 | Armstrong | |
| 2007/0283455 A1* | 12/2007 | Gray et al. | 800/278 |

FOREIGN PATENT DOCUMENTS

| | | | |
|---|---|---|---|
| CN | 1429904 | * | 7/2003 |
| EP | 0 672 752 A1 | | 9/1995 |
| EP | 1 306 440 A1 | | 5/2003 |
| JP | 26497287 B2 | | 5/1997 |
| JP | 11-290072 A | | 10/1999 |
| JP | 2000-342256 A | | 12/2000 |
| JP | 3329819 B2 | | 7/2002 |
| JP | 2002-528047 A | | 9/2002 |
| JP | 2003-274953 A | | 9/2003 |
| WO | WO-95/06722 A1 | | 3/1995 |
| WO | WO-99/38979 A1 | | 8/1999 |

OTHER PUBLICATIONS

Cheng et al. Plant Cell Reports 16(3-4): 127-132 (Dec. 1996).*
Kumar, K. K., et al., "An Improved *Agrobacterium*-Mediated Transformation Protocol for Recalcitrant Elite Indica Rice Cultivars," Plant Molecular Biology Reporter, vol. 23, No. 1, pp. 67-73, Mar. 2005. XP002522679.
Jones, Huw D. et al., "Review of methodologies and a protocol for the *Agrobacterium*-mediated transformation of wheat," Plant Methods, vol. 1, No. 1, pp. 1-9, Sep. 5, 2005. XP021011428.
Bidney, D., et al., "Microprojectile bombardment of plant tissues increases transformation frequency by *Agrobacterium tumefaciens*," Plant Mol. Biol., 18 301-313 (1992).
Chan, M-T. et al., "*Agrobacterium*-mediated production of transgenic rice plants expressing a chimeric α-amylase promoter/β-glucuronidase gene," Plant Mol. Biol., 22 491-506 (1993).
Cheng, M., et al., "Genetic Transformation of Wheat Mediated by *Agrobacterium tumefaciens*," Plant Physiol., 115 971-980 (1997).
De Cleene, M. and De Ley, J., "The Host Range of Crown Gall," Bot. Rev., 42 389-466 (1976).
Deji, A., et al., "Genomic organization and transcriptional regulation of maize *ZmRR1* and *ZmRR2* encoding cytokinin-inducible response regulators," Biochim. et Biophys. Acta, 1492 216-220 (2000).
Frame, B. R., et al., "*Agrobacterium tumefaciens*-Mediated Transformation of Maize Embryos Using a Standard Binary Vector System," Plant Physiol., 129 13-22 (2002).
Gould, J., et al., "Transformation of *Zea mays* L. Using *Agrobacterium tumefaciens* and the Shoot Apex," Plant Physiol., 95 426-434 (1991).
Grimsley, N., et al., "*Agrobacterium*-mediated delivery of infectious maize streak virus into maize plants," Nature, 325 177-179 (1987).
Hiei, Y., et al., "Efficient transformation of rice (*Oryza sativa* L.) mediated by *Agrobacterium* and sequence analysis of teh boundaries of the T-DNA," The Plant Journal, 6 271-282 (1994).
Ishida, Y., et al., "High efficiency transformation of miaze (*Zea mays* L.) mediated by *Agrobacterium tumefaciens*," Nature Biotechnology, 14, 745-750 (1996).
Ishida, Y., et al., "Improved Protocol for Transformation of Maize (*Zea mays* L.) Mediated by *Agrobacterium tumefaciens*," Plant Biotechnology, 20 57-66 (2003).
Mooney, P.A., et al., "*Agrobacterium tumefaciens*-gene transfer into wheat tissues," Plant Cell, Tissues and Organ Culture, 25 209-218 (1991).
Negrotto, D., et al., "The use of phosphomannose-isomerase as a selectable marker to recover transgenic maize plants (*Zea mays* L.) via *Agrobacterium* transformation," Plant Cell Reports, 19 798-803 (2000).
Nomura, M., et al., "The evolution of C4 plants: acquisition of *cis*-regulatory sequences in the promoter of C4-type pyruvate, orthophosphate dikinase gene," Plant J., 22 211-221 (2000).
Nomura, M., et al., "The promoter of *rbcS* in a C3 plant (rice) directs organ-specific light-dependent expression in a C4 plant (maize), but does not confer bundle sheath cell-specific expression," Plant Mol. Biol., 44 99-106 (2000).

(Continued)

*Primary Examiner* — David T Fox
(74) *Attorney, Agent, or Firm* — Birch, Stewart, Kolasch & Birch, LLP (57) ABSTRACT

The present invention provides a method for *Agrobacterium*-mediated gene transfer into a plant material, which comprises inoculating an *Agrobacterium* into the plant material in the presence of a powder. In the method of the present invention, the powder at least does not affect living tissues and has one or more properties selected from the group consisting of: being insoluble in water; having an affinity for living tissues; having adsorption properties; and having a surface polarity. The present invention also provides a method for producing a transformed plant, which comprises using the gene transfer method of the present invention.

9 Claims, 5 Drawing Sheets

OTHER PUBLICATIONS

Potrycus, I., "Gene Transfer to Cereals: An Assessment," Bio/technology, 8 535-542 (1990).

Raineri, D. M., et al., *Agrobacterium*-mediated transformation of rice (*Oryza sativa* L.) Bio/technology, 8 33-38 (1990).

Singh, N. and Chawla, S., "Use of silicon carbide for *Agrobacterium*-mediated transformation in wheat," Current Science, 76 1483-1485 (1999).

Taniguchi, M., et al., "The Promoter for the Maize $C_4$ Pyruvate, orthophosphate Dikinase Gene Directs Cell- and Tissue-specific Transcription in Transgenic Maize Plants," Plant Cell Physiol., 41 42-48 (2000).

Trick, H. N. and Finer, J. J., "SAAT: sonication-assisted *Agrobacterium*-mediated transformation," Transgenic Res., 6:329-336 (1997).

Tingay, S., et al., "*Agrobacterium tumefaciens*-mediated barley transformation," Plant J., 11 1369-1376 (1997).

Zhao, Z.-Y., et al., "*Agrobacterium*-mediated sorghum transformation," Plant Mol. Biol., 44 789-798 (2000).

Zhao, Z.-Y., et al., "High throughput genetic transformation mediated by *Agrobacterium tumefaciens* in maize," Mol. Breed., 8 323-333 (2001).

Hoekema, A., et al., "A binary plant vector strategy based on separation of vir- and T-region of the *Agrobacterium tumefaciens* Ti-plasmid," Nature, 303 179-180 (1983).

Komari, T. and Kubo, T., (1999) Methods of Genetic Transformation: *Agrobacterium tumefaciens*. In Vasil, I. K. (ed.), Molecular improvement of cereal crops, Kluwer Academic Publishers, Dordrecht, p. 43-82.

\* cited by examiner

METHOD FOR IMPROVING TRANSFORMATION EFFICIENCY USING POWDER

This application is the national stage of PCT/JP2006/324839, filed Dec. 13, 2006, which claims the benefit of priority of PCT Application No. PCT/JP2005/022863, filed Dec. 13, 2005.

TECHNICAL FIELD

The present invention relates to an efficient method for *Agrobacterium*-mediated gene transfer into plant materials.

BACKGROUND ART

Methods known for transformation of monocotyledons such as maize and rice, which are major grain crops, include electroporation, particle gun transformation, etc. However, these physical gene transfer methods have problems in that genes are introduced as multiple copies or are not inserted in an intact state, and the resulting transformed plants may often show abnormal in morphology and sterility.

*Agrobacterium*-mediated gene transfer is a method for plant transformation based on functions of *Agrobacterium*. A soil bacterium *Agrobacterium* (*Agrobacterium tumefaciens*) functions in such a manner that the T-DNA forming a part of its Ti (tumor-inducing) plasmid involved in the pathogenicity of the *Agrobacterium* is integrated into the genome of a plant when it infects the plant. *Agrobacterium*-mediated plant transformation is a method for introducing a desired gene into the genome of a plant through the above *Agrobacterium* function by constructing a transforming plasmid in which the T-DNA region of the Ti plasmid is replaced by the gene desired to be introduced into the plant genome and then using *Agrobacterium* prepared to carry the transforming plasmid in place of the Ti plasmid.

*Agrobacterium*-mediated gene transfer is universally used as a transformation method for dicotyledons. Although it has been understood that hosts of *Agrobacterium* are limited only to dicotyledons and *Agrobacterium* has no ability to infect monocotyledons (De Cleene, M. and De Ley, J., (1976) Bot. Rev., 42: 389-466), some attempts have been made to transform monocotyledons through *Agrobacterium*-mediated method (Grimsley, N., et al., (1987) Nature, 325: 177-179; Gould, J., et al., (1991) Plant Physiol., 95: 426-434; Mooney, P. A., et al., (1991) Plant Cell, Tissues and Organ Culture, 25: 209-218; Raineri, D. M., et al., (1990) Bio/technology, 8: 33-38). These study reports suggested that *Agrobacterium*-mediated gene transfer is also possible for Gramineae crops including rice, maize and wheat, but the reports failed to show persuasive results because these studies had a problem in reproducibility and were also insufficient for transgene confirmation (Potrycus, I., (1990) Bio/technology, 8: 535-542).

Chan et al. injured immature rice embryos, which had been cultured for 2 days in the presence of 2,4-D (2,4-dichlorophenoxyacetic acid), and then inoculated these embryos with *Agrobacterium* carrying genes for nptII and GUS in a medium containing suspension-cultured potato cells. They cultured the thus treated immature embryos on G418-containing medium to obtain regenerated plants from the induced calli. They confirmed the location of the GUS gene in the regenerated plants and their progeny by Southern analysis, and reported that the presence of the transgene was observed in both T0 generation of regenerated plants and their progeny (Chan, M-T., et al., (1993) Plant Mol. Biol., 22: 491-506). This result supports *Agrobacterium*-mediated transformation in rice, but the transformation efficiency was as low as 1.6%. Moreover, there was only one regenerated plant that showed normal growth, although 250 immature embryos were used for testing. Since laborious efforts are required to excise immature embryos of rice, such low transformation efficiency is not practical.

In recent years, it has been reported that stable and highly efficient transformation is also possible in monocotyledons including rice and maize when using a super-binary vector carrying a part of the virulence gene from super-virulent *Agrobacterium* (Hiei, Y., et al., (1994) The Plant Journal, 6: 271-282; Ishida, Y., et al., (1996) Nature Biotechnology, 14: 745-750). These reports suggest that *Agrobacterium*-mediated transformation not only allows stable and highly efficient transformation, but is also advantageous in that the resulting transformed plants have fewer mutations, and in that the introduced genes are low in copy number and are often in an intact state. Following success in rice and maize, further reports were issued for *Agrobacterium*-mediated transformation in other major grain crops, i.e., wheat (Cheng, M., et al., (1997) Plant Physiol., 115: 971-980), barley (Tingay, S., et al., (1997) Plant J., 11: 1369-1376) and sorghum (Zhao, Z.-Y., et al., (2000) Plant Mol. Biol., 44: 789-798).

Ishida et al. used maize inbred line A188 and A188-related inbred lines as materials to perform *Agrobacterium*-mediated transformation (Ishida, Y., et al., (1996) Nature Biotechnology, 14: 745-750). Thereafter, further reports were issued for *Agrobacterium*-mediated transformation in maize, each of which reports used A188 and A188-related hybrids (Deji, A., et al., (2000) Biochim. et Biophys. Acta, 1492: 216-220; Negrotto, D., et al., (2000) Plant Cell Reports, 19: 798-803; Nomura, M., et al., (2000) Plant J., 22: 211-221; Nomura, M., et al., (2000) Plant Mol. Biol., 44: 99-106; Taniguchi, M., et al., (2000) Plant Cell Physiol., 41: 42-48; Zhao, Z.-Y., et al., (2001) Mol. Breed., 8: 323-333; Frame, B. R., et al., (2002) Plant Physiol., 129: 13-22). Attempts which have been made to improve the efficiency of *Agrobacterium*-mediated maize transformation include: selection of transformed cells on N6 basal medium (Zhao, Z.-Y., et al., (2001) Mol. Breed., 8: 323-333); addition of $AgNO_3$ and carbenicillin to culture medium (Zhao, Z.-Y., et al., (2001) Mol. Breed., 8: 323-333; Ishida, Y., et al., (2003) Plant Biotechnology, 20: 57-66); and addition of cysteine to co-culture medium (Frame, B. R., et al., (2002) Plant Physiol., 129: 13-22). Ishida et al. selected co-cultured immature maize embryos on a medium containing $AgNO_3$ and carbenicillin to produce transformed plants from inbred lines H99 and W117, which are publicly available inbred other than A188, and also reported that this procedure improved the transformation efficiency in A188 (Ishida, Y., et al., (2003) Plant Biotechnology, 20: 57-66).

Singh and Chawla reported that immature wheat embryos expressing the GUS gene increased in number when mixed in a suspension of silicon carbide fibers (SCFs) with a vortex mixer for 2 to 3 minutes before being inoculated with *Agrobacterium* (Singh, N. and Chawla, S., (1999) Current Science, 76: 1483-1485). This is because the immature embryos were injured by SCFs. Other attempts to injure tissues before *Agrobacterium* inoculation include injuring with a particle gun (Bidney et al., 1992) and injuring by ultrasonication (Trick, H. N. and Finer, J. J., (1997) Transgenic Res., 6:329-336).

Various attempts have been made to improve the transformation efficiency in *Agrobacterium*-mediated maize transformation (Negrotto, D., et al., (2000) Plant Cell Reports, 19: 798-803; Zhao, Z.-Y., et al., (2001) Mol. Breed., 8: 323-333; Frame, B. R., et al., (2002) Plant Physiol., 129: 13-22; Ishida, Y., et al., (2003) Plant Biotechnology, 20: 57-66). However, the resulting effects are still low when compared to rice which is also a member of monocotyledons, so that further improvement in the transformation efficiency is desired not only for production of practical transformed maize plants, but also for confirmation of novel genes for their effect in maize. Moreover, in response to recent progress in genomics studies, the necessity of transformation has been increased for the purpose of gene function analysis. Thus, there will be a demand for efficient transformation systems.

Likewise, the development of a method achieving higher transformation efficiency in other monocotyledons and dicotyledons than that provided by current procedures is also useful in various instances where transformants are used.

All documents cited herein are incorporated herein by reference in their entirety.

Patent Document 1: Japanese Patent No. 2,649,287
Patent Document 2: Japanese Patent No. 3,329,819
Patent Document 3: Japanese Patent Public Disclosure No. 2000-342256
Patent Document 4: International Publication No. WO 95/06722
Non-patent Document 1: Bidney, D., et al., (1992) Plant Mol. Biol., 18: 301-313.
Non-patent Document 2: Chan, M-T., et al., (1993) Plant Mol. Biol., 22: 491-506.
Non-patent Document 3: Cheng, M., et al., (1997) Plant Physiol., 115: 971-980.
Non-patent Document 4: De Cleene, M. and De Ley, J., (1976) Bot. Rev., 42: 389-466.
Non-patent Document 5: Deji, A., et al., (2000) Biochim. et Biophys. Acta, 1492: 216-220.
Non-patent Document 6: Frame, B. R., et al., (2002) Plant Physiol., 129: 13-22.
Non-patent Document 7: Gould, J., et al., (1991) Plant Physiol., 95: 426-434.
Non-patent Document 8: Grimsley, N., et al., (1987) Nature, 325: 177-179.
Non-patent Document 9: Hiei, Y., et al., (1994) The Plant Journal, 6: 271-282.
Non-patent Document 10: Ishida, Y., et al., (1996) Nature Biotechnology, 14: 745-750.
Non-patent Document 11: Ishida, Y., et al., (2003) Plant Biotechnology, 20: 57-66.
Non-patent Document 12: Mooney, P. A., et al., (1991) Plant Cell, Tissues and Organ Culture, 25: 209-218.
Non-patent Document 13: Negrotto, D., et al., (2000) Plant Cell Reports, 19: 798-803.
Non-patent Document 14: Nomura, M., et al., (2000) Plant J., 22: 211-221.
Non-patent Document 15: Nomura, M., et al., (2000) Plant Mol. Biol., 44: 99-106.
Non-patent Document 16: Potrycus, I., (1990) Bio/technology, 8: 535-542.
Non-patent Document 17: Raineri, D. M., et al., (1990) Bio/technology, 8: 33-38.
Non-patent Document 18: Singh, N. and Chawla, S., (1999) Current Science, 76: 1483-1485.
Non-patent Document 19: Taniguchi, M., et al., (2000) Plant Cell Physiol., 41: 42-48.
Non-patent Document 20: Trick, H. N. and Finer, J. J., (1997) Transgenic Res., 6:329-336.
Non-patent Document 21: Tingay, S., et al., (1997) Plant J., 11: 1369-1376.
Non-patent Document 22: Zhao, Z.-Y., et al., (2000) Plant Mol. Biol., 44: 789-798.
Non-patent Document 23: Zhao, Z.-Y., et al., (2001) Mol. Breed., 8: 323-333.
Non-patent Document 24: Hoekema, A., et al., (1983) Nature, 303: 179-180
Non-patent Document 25: Komari, T. and Kubo, T., (1999) Methods of Genetic Transformation: *Agrobacterium tumefaciens*. In Vasil, I. K. (ed.), Molecular improvement of cereal crops, Kluwer Academic Publishers, Dordrecht, p. 43-82.

DISCLOSURE OF THE INVENTION

Problems to be Solved by the Invention

An object of the present invention is to develop and provide a method which allows gene transfer into plants at higher efficiency than that achieved by conventional methods for *Agrobacterium*-mediated gene transfer into plants, i.e., a method which allows transformation at higher efficiency than that achieved conventionally. Another object of the present invention is to develop and provide a method for producing a transformed plant, which is based on the above method.

Means for Solving the Problems

As a result of extensive and intensive efforts made to solve the problems stated above, the inventors of the present invention have found that when *Agrobacterium*-mediated gene transfer into a plant material is performed in the presence of a powder, gene transfer is achieved at higher efficiency than in the absence of a powder. The inventors have further performed transformant selection on the gene-transferred plant materials, and thus have found that the transformation efficiency is improved in plant materials which were gene-transferred in the presence of a powder, as compared to those obtained in the absence of a powder. The present invention therefore provides a method for improving gene transfer efficiency and/or transformation efficiency by inoculating an *Agrobacterium* into a plant material in the presence of a powder.

Method for Gene Transfer Using Powder

The present invention relates to a method for *Agrobacterium*-mediated gene transfer into a plant material, which comprises inoculating an *Agrobacterium* into the plant material in the presence of a powder.

In the method of the present invention, the phrase "in the presence of a powder" means a state where a powder is present during inoculation of an *Agrobacterium* into a plant material. For this purpose, an *Agrobacterium* suspension may be pre-mixed with a powder and the resulting mixture may then be inoculated into a plant material; or a plant material may be pre-mixed with a powder and the resulting mixture may then be inoculated with an *Agrobacterium*; or an *Agrobacterium* suspension, a powder and a plant material may be mixed at a time to thereby inoculate the *Agrobacterium* into the plant material. In the present invention, it is enough that the elements are mixed to give a moderately uniform mixture, and there is no necessity to vigorously shake the elements. For example, in a case where shaking instrument with a relatively strong power (e.g., a vortex mixer) is used for mixing purposes, the mixing time is set to be short, for example, 1 minute or less, preferably 45 seconds or less, and more preferably 30 seconds or less.

Thus, in one embodiment, the method of the present invention is a method for *Agrobacterium*-mediated gene transfer into a plant material, which comprises the step of inoculating an *Agrobacterium* into the plant material in the presence of a powder, wherein the step comprises:

(1) mixing an *Agrobacterium* suspension with the powder; and (2) inoculating the mixture from (1) into the plant material.

In another embodiment, the method of the present invention is a method for *Agrobacterium*-mediated gene transfer into a plant material, which comprises the step of inoculating an *Agrobacterium* into the plant material in the presence of a powder, wherein the step comprises:

(1) mixing the plant material with the powder; and (2) inoculating the mixture from (1) with an *Agrobacterium* suspension.

In yet another embodiment, the method of the present invention is a method for *Agrobacterium*-mediated gene transfer into a plant material, which comprises the step of inoculating an *Agrobacterium* into the plant material in the presence of a powder, wherein the step comprises mixing together an *Agrobacterium* suspension, the powder and the plant material to thereby inoculate the *Agrobacterium* into the plant material.

The method of the present invention is based on a technical idea that the surface of a powder, which was added during inoculation of an *Agrobacterium* into a plant material, provides a reaction field required for infection of the *Agrobacterium* into the plant material, thereby resulting in improved infection efficiency and hence improved gene transfer and transformation efficiencies. Thus, in the method of the present invention, such a powder at least does not affect living tissues and has one or more properties selected from the group consisting of: being insoluble in water; having an affinity for living tissues; having adsorption properties; and having a surface polarity. Preferably, the powder used in the method of the present invention has two or more of the above four properties. More preferably, the powder used in the method of the present invention does not affect living tissues, is insoluble in water, and optionally further has one or more properties selected from the group consisting of: having an affinity for living tissues; having adsorption properties; and having a surface polarity.

The expression "not affect living tissues" means having no inhibitory effect on vital activities of plants and *Agrobacterium* cells. In the method of the present invention, the powder is available for use as long as it is free from toxic or other properties which substantially produce adverse effects on each stage including transformation, regeneration after transformation, or growth after regeneration.

The expression "being insoluble in water" means being insoluble or sparingly soluble in an aqueous solvent, more specifically means being insoluble or sparingly soluble in a buffer or medium to be used in the method of the present invention, and even more specifically means being insoluble or sparingly soluble under conditions used for preparation of an *Agrobacterium* suspension and a plant material as well as under conditions used for inoculation. Due to its water insolubility, the powder used in the method of the present invention can maintain its powder form without being dissolved during each step in the method of the present invention.

The expression "having an affinity for living tissues" means having an adsorption capacity for living tissues. Since particles having an affinity for living tissues are capable of adsorbing *Agrobacterium* cells and/or a plant material, the surface of such particles may provide a reaction field for efficient infection.

The expression "having adsorption properties" means the ability to adsorb a substance. In the method of the present invention, *Agrobacterium* cells and/or a plant material may be adsorbed to the added powder, whereby the powder surface may provide a reaction field for infection. Examples of a powder having adsorption properties include porous powders.

The expression "having a surface polarity" means that the powder surface is polar, i.e., the powder surface is relatively hydrophilic. Such a powder having a surface polarity can form a water membrane on the powder surface to thereby contain *Agrobacterium* cells and/or a plant material within this water membrane.

Powders that can be used in the method of the present invention are exemplified by those selected from the group consisting of, but not limited to, porous ceramics, glass wool, activated charcoal, and mixtures thereof. Examples of porous ceramics include, but are not limited to, hydroxyapatite, silica gel and zeolite.

Powders that can be used in the method of the present invention have, but are not limited to, a particle size of 1 to 150 μm, preferably 5 to 75 μm. Powders having these particle sizes can be obtained, e.g., by sizing with sieves or various classifiers, or alternatively, are also generally commercially available. It should be noted that particle size determination may be accomplished by using laser diffraction or an optical microscope, etc.

The powder amount used in the method of the present invention is set at, but not limited to, an amount such that the concentration of an *Agrobacterium* inoculated into a plant material is 30 mg/ml or more, preferably 60 mg/ml or more. The upper limit of the powder amount used in the method of the present invention is set at, but not limited to, an amount such that the concentration of an *Agrobacterium* inoculated into a plant material is 240 mg/ml or less.

In the method of the present invention, inoculation of an *Agrobacterium* into a plant material may be accomplished by simply establishing contact between the plant material and the *Agrobacterium*. Inoculation may be accomplished by either standard inoculation or drop inoculation. Standard inoculation is a technique in which a plant material is mixed with an *Agrobacterium* suspension (inoculum) to immerse the plant material in the suspension, and the immersed plant material is collected and plated onto a medium to effect co-culture for inoculation. Drop inoculation is a technique in which an *Agrobacterium* suspension is added dropwise onto a plant material plated on a medium, and after the suspension added dropwise is dried, the plant material is transferred to another site on the same medium or plated onto another medium to effect co-culture for inoculation.

The period of co-culture may be, but is not limited to, 1 hour or more, preferably 1 day or more, 3 days or more, or 7 days or more. The upper limit of the co-culture period is preferably, but is not limited to, 7 days or less, 10 days or less, or 14 days or less.

In the method of the present invention, the time for mixing of a powder, an *Agrobacterium* suspension and a plant material or mixing of an *Agrobacterium* suspension and a plant material is not limited in any way, as long as these elements are fully mixed. A preferred mixing time may be 3 minutes, 5 minutes, 10 minutes or 30 minutes.

Plants for use in the method of the present invention include both monocotyledons and dicotyledons. Monocotyledons include, but are not limited to, rice, maize, barley, wheat, asparagus, sorghum and sugar cane. Dicotyledons include, but are not limited to, tobacco, soybean, Bird's foot trefoil, potato, cotton and sunflower. A preferred plant for use in the method of the present invention is a monocotyledon, most preferably rice or maize.

In the method of the present invention, the term "plant material" is intended to encompass all aspects of plants to be used for *Agrobacterium*-mediated transformation of plants including plant cells, leaves, roots, stems, buds, flowers (including stamens and pistils, etc.), fruits, seeds, germinated seeds or plant tissues of any other parts, meristem, explants, immature embryos, calli or embryoid-like tissues (hereinafter referred to as calli or the like, or simply calli), or whole plants. A desirable plant form used in the method of the present invention is an immature embryo or a callus, most desirably an immature embryo.

Method for Producing Transformed Plant Based on Gene Transfer Method Using Powder The present invention also provides a method for producing a transformed plant, which is based on the above gene transfer method.

The present invention relates to a method for producing a transformed plant through *Agrobacterium*-mediated transformation in a plant material, which comprises the following steps:

(1) inoculating an *Agrobacterium* suspension into the plant material in the presence of a powder;
(2) selecting a transformed plant material; and
(3) regenerating the selected transformant.

In one embodiment of the present invention, step (1) is accomplished by:

(i) mixing the *Agrobacterium* suspension with the powder; and
(ii) inoculating the mixture from (i) into the plant material.

In another embodiment of the present invention, step (1) is accomplished by:

(i) mixing the plant material with the powder; and
(ii) inoculating the mixture from (i) with the *Agrobacterium* suspension.

In yet another embodiment of the present invention, step (1) is accomplished by mixing together the *Agrobacterium* suspension, the powder and the plant material to thereby inoculate the *Agrobacterium* into the plant material.

The properties, material, particle size and amount of a powder that can be used in the method of the present invention for producing a transformed plant are the same as described above for the method of the present invention for gene transfer in a plant.

Likewise, in the method of the present invention for producing a transformed plant, inoculation of plant cells with an *Agrobacterium* suspension may be accomplished by using the same technique, mixing time and co-culture period as described above.

Moreover, in the method of the present invention for producing a transformed plant, a transformed plant to be produced is the same as the plant available for use in the gene transfer method of the present invention.

Methods for *Agrobacterium*-Mediated Gene Transfer and Transformation

*Agrobacterium*-mediated gene transfer typically comprises the following steps:

(a) preparing a plant material;
(b) preparing an *Agrobacterium* carrying a vector containing a desired transgene; and
(c) infecting the plant material prepared in step (a) with the *Agrobacterium* prepared in step (b).

In order to obtain a transformant, step (c) may be further followed by the steps of:

(d) selecting a transformed cell; and
(e) optionally regenerating the selected transformant.

Specifically, for monocotyledons, it is possible to use a method characterized in that the plant material is cultured in a medium containing auxin (e.g., 2,4-D (2,4-dichlorophenoxyacetic acid)) or cytokinin or the like to turn it into a dedifferentiated state or a state under dedifferentiation in step (a) and infected with *Agrobacterium* in step (c) as described in a document (Japanese Patent No. 2,649,287); or a method characterized in that an immature embryo of the plant is used as the plant material and cultured in a medium containing auxin (e.g., 2,4-D) or cytokinin or the like in step (c) without dedifferentiating it in step (a) as described in a document (Japanese Patent No. 3,329,819).

Step (a)

The "plant" used herein for gene transfer is intended to include both monocotyledons and dicotyledons. Monocotyledons for use in the method of the present invention include, but are not limited to, rice, maize, barley, wheat, asparagus, sorghum and the like. Dicotyledons for use in the method of the present invention include, but are not limited to, tobacco, soybean, Bird's foot trefoil, potato, cotton, sunflower and the like. A preferred plant for use in the method of the present invention is a monocotyledon, most preferably rice or maize.

The term "plant material" is intended to encompass all aspects of plants to be used for *Agrobacterium*-mediated transformation of plants including, but not limited to, plant cells, leaves, roots, stems, buds, flowers (including stamens and pistils, etc.), fruits, seeds, germinated seeds or plant tissues of any other parts, meristem, explants, immature embryos, calli, or whole plants.

A desirable plant form used in the method of the present invention is an immature embryo or a callus, most desirably an immature embryo. As used herein, the expressions of plant cell, tissue and whole plant have the same meanings as commonly used in the art. As used herein, the immature embryo means the embryo of an immature seed under maturation after pollination. The stage (maturation phase) of the immature embryo used in the method of the present invention are not specifically limited, and it may be excised at any stage after pollination. However, it is preferably at a post-pollination stage of two days or more. Preferred for use is the scutellum of an immature embryo capable of inducing a callus that can be dedifferentiated to regenerate a normal plant by the method described below after the transformation described below. The immature embryo is preferably an immature embryo of an inbred line, F1 between inbred lines, F1 between an inbred line and an open-pollinated cultivar, or a commercially available F1 cultivar. As used herein, a callus means an undifferentiated cell clump under uncontrolled growth. A callus can be obtained by culturing a differentiated cell of a plant tissue in a medium containing a plant growth regulator such as auxin (e.g., 2,4-D) or cytokinin (referred to as dedifferentiation medium). The treatment for obtaining a callus is called dedifferentiation treatment and this process is called dedifferentiation process.

In step (a), a material suitable for transformation is prepared by excising a plant tissue, immature embryo or the like as appropriate from a plant, seed or the like. Optionally, the plant material may be cultured before being infected with an *Agrobacterium*.

Step (b)

A soil bacterium *Agrobacterium* (*Agrobacterium tumefaciens*) has long been known to induce crown gall disease in many dicotyledons, and in 1970s, it was discovered that its Ti plasmid is involved in pathogenicity and that the T-DNA forming a part of the Ti plasmid is integrated into plant genomes. Subsequently, it was shown that the T-DNA contains genes involved in the synthesis of hormones necessary for inducing cancers (cytokinin and auxin) and that these genes are expressed in plants though they are bacterial genes. Excision of the T-DNA and its transfer to plants require genes existing in the virulence region (vir region) on the Ti plasmid, and excision of the T-DNA requires border sequences flanking the T-DNA. Another *Agrobacterium*, *Agrobacterium rhizogenes* has a similar system based on its Ri plasmid (e.g., FIGS. 3 and 4 of Japanese Patent Public Disclosure No. 2000-342256).

A desired gene was expected to be integrated into plant genomes by inserting it onto the T-DNA because the T-DNA is integrated into plant genomes by infection with *Agrobacterium*. However, it was difficult to insert a gene onto the T-DNA on the Ti plasmid by standard genetic engineering techniques because the Ti plasmid is as large as 190 kb or more. Thus, a method for inserting an exogenous gene onto the T-DNA was developed.

Initially, disarmed strains in which the hormone-synthesizing genes have been removed from the T-DNA of the tumor-inducing Ti plasmid such as LBA4404 (see Hoekema, A., et al., (1983), Nature, Vol. 303, p. 179-180), C58C1 (pGV3850), and GV3Ti11SE were prepared. Two methods were developed for introducing a desired gene into the T-DNA of the Ti plasmid of *Agrobacterium* or introducing the T-DNA carrying a desired gene into *Agrobacterium* using these strains. The first method is called the intermediate vector method wherein an intermediate vector that can be easily genetically manipulated to insert a desired gene and that can be replicated in *E. coli* is inserted into the T-DNA region of a disarmed Ti plasmid of *Agrobacterium* by homologous recombination via triparental mating.

The second method is called the binary vector method based on the finding that the vir region is required for integration of the T-DNA into plants but need not be present on the same plasmid to serve its functions. There exist virA, virB, virC, virD, virE and virG in the vir region (Dictionary of Plant Biotechnology, published by Enterprise (1989)), and the vir region refers to a region containing all of these virA, virB, virC, virD, virE and virG. A binary vector which is a small plasmid replicable in both *Agrobacterium* and *E. coli* into which the T-DNA is integrated, is introduced into *Agrobacterium* having a disarmed Ti plasmid.

Introduction of a binary vector into *Agrobacterium* can be performed by known methods such as electroporation and triparental mating. Binary vectors include pBIN19, pBI121, pGA482, etc., and many novel binary vectors based on them were constructed and used for transformation. In the Ri plasmid system, similar vectors were constructed and used for transformation.

*Agrobacterium* A281 is a super-virulent strain that has a wide host range and higher transformation efficiency than those of other strains. This characteristic is attributed to pTiBo542 of the Ti plasmid carried by A281. Two novel systems were developed using pTiBo542 until now. One uses EHA101 and EHA105 strains carrying a disarmed Ti plasmid of pTiBo542 and finds applications in transformation of various plants as a system having a high transforming ability by applying these strains to the binary vector system described above.

The other is a 'super-binary' vector (see Hiei, Y., et al., (1994), The Plant Journal, Vol. 6, p. 271-282; Ishida, Y., et al., (1996), Nature Biotechnology, Vol. 4, p. 745-750; Komari, T. and Kubo T., (1999), Methods of Genetic Transformation: *Agrobacterium tumefaciens*. In Vasil, I. K. (ed.) Molecular improvement of cereal crops., Kluwer Academic Publishers, Dordrecht, p. 43-82; and International Publication No. WO 95/06722) system (e.g., FIG. 4 of Japanese Patent Public Disclosure No. 2000-342256). This system is a kind of binary vector system because it consists of a disarmed Ti plasmid having the vir region (virA, virB, virC, virD, virE and virG (hereinafter sometimes each referred to as "vir fragment region")) and a plasmid having the T-DNA. However, it differs in that it uses a super-binary vector in which a fragment of the vir region substantially deprived of at least one of the vir fragment regions (preferably the fragment including at least virB or virG, more preferably the fragment including virB and virG) is integrated, as the plasmid having the T-DNA, i.e., a binary vector. Homologous recombination via triparental mating can be used as a convenient method for introducing the T-DNA region containing a desired gene into *Agrobacterium* carrying a super-binary vector.

*Agrobacterium* that can be used as hosts in the method of the present invention are not specifically limited, but preferably include *Agrobacterium tumefaciens* (e.g., *Agrobacterium tumefaciens* LBA4404 (see Hoekema, A., et al., (1983), Nature, Vol. 303, p. 179-180) and EHA101 as described above).

According to the method of the present invention, significant effects can be obtained, without specific limitation, by using any gene transfer system based on the expression of the genes in the virulence (vir) region in *Agrobacterium*. Thus, benefits of the present invention can be obtained by using any vector system such as intermediate vectors, binary vectors, super-virulent binary vectors and super-binary vectors as described above. The same effects can also be obtained by using different vector systems obtained by modifying these vectors (e.g., by excising a part or all of the vir region of *Agrobacterium* and additionally inserting it into a plasmid, or excising a part or all of the vir region and introducing it as a part of a novel plasmid into *Agrobacterium*). According to the method of the present invention, the infection efficiency can also be virtually improved with wild-type *Agrobacterium* by increasing the introduction efficiency of the wild-type T-DNA region into plants.

A desired gene to be introduced into plants can be inserted at a restriction enzyme site in the T-DNA region of the plasmid described above according to standard procedures, and can be selected on the basis of a suitable selective marker such as a gene having resistance to a drug such as PPT (phosphinothricin), hygromycin, kanamycin or paromomycin simultaneously or separately inserted into the plasmid. A desired DNA may not be readily inserted into the T-DNA region of a large plasmid having many restriction enzyme sites by conventional subcloning methods. In such cases, the desired DNA can be inserted by homologous recombination in cells of *Agrobacterium* via triparental mating. The size of the transgene is not limited, but preferably about 100 by to 200 kbp.

Introduction of the plasmid into an *Agrobacterium* such as *Agrobacterium tumefaciens* can be accomplished by conventional methods such as triparental mating as described above, electroporation, electroinjection, and chemical treatments with PEG or the like.

The gene to be introduced into plants is basically located between the left and right border sequences flanking the T-DNA in the same manner as in conventional techniques. However, only one border sequence may exist because the plasmid is circular, or three or more border sequences may exist when multiple genes are to be located at different sites. The gene may also be located on the Ti or Ri plasmid or on another plasmid in *Agrobacterium*. Alternatively, it may also be located on multiple types of plasmids.

Step (c)

*Agrobacterium*-mediated gene transfer can be performed simply by contacting a plant material with an *Agrobacterium*. For example, it can be performed by preparing an *Agrobacterium* suspension having a cell density of about $10^6$ to $10^{11}$ cfu/ml, immersing a plant material in this suspension for about 3 to 10 minutes, and then co-culturing them on a solid medium for several days.

Preferably, the plant material is co-cultured with *Agrobacterium* at the same time the plant material is infected with *Agrobacterium* or before *Agrobacterium* is removed after infection. Known media can be used for co-culture. For example, LS-AS medium and nN6-As medium used in the Example section below or other media such as N6S3-AS medium and 2N6-AS medium (see Hiei, Y., et al., (1994), The Plant Journal, Vol. 6, p. 271-282) are known.

In comparison with standard *Agrobacterium*-mediated gene transfer/transformation, the method of the present invention is characterized in that step (c), i.e., infection of a plant material with *Agrobacterium* is performed in the presence of a powder.

Steps (d) and (e)

In order to obtain a transformant if desired, step (c) described above should be followed by the steps of:
(d) selecting a transformed cell; and
(e) optionally regenerating the selected transformant.

That is, in order to perform transformation of a plant, it is typically necessary to select a plant cell containing an exogenous gene stably integrated into the chromosome after the exogenous gene is introduced into the plant cell.

The step of selecting a transformed cell means selecting a cell having a desired trait based on phenotype data and/or physical data.

Phenotype data such as transformation efficiency can be obtained by evaluating the expression of a marker gene and/or a selective marker gene co-introduced with a gene desired to be introduced into a plant. Marker genes and/or selective marker genes that can be used include, e.g., the GUS (β-glucuronidase) gene and/or antibiotic resistance genes (e.g., PPT (phosphinothricin) resistance genes, hygromycin resistance genes, kanamycin resistance genes, paromomycin resistance genes)), etc. When the GUS gene is used as a marker gene, transformation efficiency can be evaluated from the coloration resulting from the cleavage of X-Gulc (5-bromo-4-chloro-3-indolyl-β-D-glucuronic acid) by GUS. When a gene resistant to an antibiotic is used as a selective marker gene, evaluation can be made from the extent of growth on a selective medium containing the antibiotic after transformation.

To ascertain that the exogenous gene has been stably integrated into the chromosome, physical data such as Southern blotting may be obtained. The selecting step may also be performed based on transmission to progeny via sexual reproduction and genetic and molecular analyses in progeny populations.

Optionally, the selected transformant may be regenerated and the regenerated plant may be grown to a whole plant. Regeneration from the selected transformant to a whole plant can be performed by known methods (e.g., Hiei, Y., et al., (1994), The Plant Journal, Vol. 6, p. 271-282; and Ishida, Y., et al., (1996), Nature Biotechnology, Vol. 4, p. 745-750).

The method of the present invention improves gene transfer efficiency and/or transformation efficiency when *Agrobacterium*-mediated gene transfer into a plant material is performed in the presence of a powder, as compared to in the absence of a powder. Gene transfer efficiency can be evaluated by, e.g., assessing the area of transient expression of the transgene. In the Example section below, transient expression of the GUS gene in immature embryos was evaluated.

Transformation efficiency can be calculated by, e.g., counting the number of regenerated plants expressing the GUS gene as transformants among those obtained from inoculated immature embryos and dividing the total number by the number of inoculated immature embryos. Alternatively, it can also be calculated by counting the number of regenerated plants showing resistance against a selective pressure as transformants and dividing the total number by the number of inoculated immature embryos.

As described above, the method of the present invention is characterized in that step (c), i.e., infection of a plant material with *Agrobacterium* is performed in the presence of a powder. It would therefore be understood that the gene transfer and/or transformation method of the present invention may be described as follows.

The method of the present invention is a method for *Agrobacterium*-mediated gene transfer and/or transformation in a plant, which comprises the following steps:
(a) preparing a plant material;
(b) preparing an *Agrobacterium* carrying a vector containing a desired transgene; and
(c) in the presence of a powder, infecting the plant material prepared in step (a) with the *Agrobacterium* prepared in step (b);
wherein the method optionally comprises the following steps subsequent to step (c) in order to obtain a transformant:
(d) selecting a transformed cell; and
(e) optionally regenerating the selected transformant.

In one embodiment, the method of the present invention is a method for *Agrobacterium*-mediated gene transfer and/or transformation in a plant, which comprises the following steps:
(a) preparing a plant material;
(b) preparing an *Agrobacterium* carrying a vector containing a desired transgene;
(c-1) mixing a suspension of the *Agrobacterium* prepared in step (b) with a powder; and
(c-2) inoculating the mixture from step (c-1) into the plant material prepared in step (a) to thereby infect the plant material with the *Agrobacterium*;
wherein the method optionally comprises the following steps subsequent to step (c-2) in order to obtain a transformant:
(d) selecting a transformed cell; and
(e) optionally regenerating the selected transformant.

In another embodiment, the method of the present invention is a method for *Agrobacterium*-mediated gene transfer and/or transformation in a plant, which comprises the following steps:
(a) preparing a plant material;
(b) preparing an *Agrobacterium* carrying a vector containing a desired transgene;
(c-1) mixing the plant material prepared in step (a) with a powder; and
(c-2) inoculating the mixture from step (c-1) with a suspension of the *Agrobacterium* prepared in step (b) to thereby infect the plant material with the *Agrobacterium*;
wherein the method optionally comprises the following steps subsequent to step (c-2) in order to obtain a transformant:
(d) selecting a transformed cell; and
(e) optionally regenerating the selected transformant.

In yet another embodiment, the method of the present invention is a method for *Agrobacterium*-mediated gene transfer and/or transformation in a plant, which comprises the following steps:
(a) preparing a plant material;
(b) preparing an *Agrobacterium* carrying a vector containing a desired transgene; and (c) mixing together the plant material prepared in step (a), a suspension of the *Agrobacterium* prepared in step (b) and a powder to thereby infect the plant material with the *Agrobacterium*;

wherein the method optionally comprises the following steps subsequent to step (c) in order to obtain a transformant:

(d) selecting a transformed cell; and (e) optionally regenerating the selected transformant.

The properties, material, particle size and amount of a powder that can be used in the method of the present invention for gene transfer and/or transformation in a plant are the same as described above for the method of the present invention for gene transfer in a plant.

Likewise, in the method of the present invention for gene transfer and/or transformation in a plant, inoculation of plant cells with an *Agrobacterium* suspension may be accomplished by using the same technique, mixing time and co-culture period as described above.

Moreover, in the method of the present invention for gene transfer and/or transformation in a plant, a transformed plant to be produced is the same as the plant available for use in the gene transfer method of the present invention.

Advantages of the Invention

It has been found that when *Agrobacterium* (inoculum) is inoculated into a plant material in the presence of a powder, gene transfer is achieved at higher efficiency than in conventional methods performed in the absence of a powder. It has also been confirmed that this method improves the formation rate of transformed calli and the production efficiency of transformed plants. The present invention therefore provides a method for *Agrobacterium*-mediated gene transfer and transformation in a plant, which achieves high efficiency for gene transfer and transformation.

BRIEF DESCRIPTION OF DRAWINGS

FIG. 3 is a graph showing the effect of powder amount on transient expression of a transgene in rice. Ten immature embryos were inoculated for each test. The vertical axis represents expression of the GUS gene in the immature embryos. The value is evaluated as follows: co-cultured immature embryos are stained with X-Gluc and then classified into the following levels: 3 (immature embryos showing GUS gene expression in 75% or more of their scutellum); 2 (immature embryos showing GUS gene expression in 25% to 74% of their scutellum); 1 (immature embryos showing GUS gene expression in 5% to 24% of their scutellum); 0.5 (immature embryos showing GUS gene expression in less than 5% of their scutellum); and 0 (immature embryos showing no GUS gene expression). The horizontal axis represents the powder amount added.

FIG. 5 is a graph showing the effect of zeolite on transient expression of a transgene in rice. Fourteen to fifteen immature embryos were inoculated for each test. The vertical axis represents expression of the GUS gene in the immature embryos. The value is evaluated as follows: co-cultured immature embryos are stained with X-Gluc and then classified into the following levels: 3 (immature embryos showing GUS gene expression in 25% or more of their scutellum); 2 (immature embryos showing GUS gene expression in 10% to 24% of their scutellum); 1 (immature embryos showing GUS gene expression in less than 10% of their scutellum); and 0 (immature embryos showing no GUS gene expression). The horizontal axis represents the particle size of zeolite added. "None" represents a control treated in the absence of any powder.

FIG. 6 is a graph showing the effect of powder addition (mixed into an inoculum) on transient expression of a transgene. Twelve to thirteen immature embryos were inoculated for each test. The vertical axis represents expression of the GUS gene in the immature embryos. The value is evaluated as follows: co-cultured immature embryos are stained with X-Gluc and then classified into the following levels: 3 (immature embryos showing GUS gene expression in 75% or more of their scutellum); 2 (immature embryos showing GUS gene expression in 25% to 74% of their scutellum); 1 (immature embryos showing GUS gene expression in 5% to 24% of their scutellum); 0.5 (immature embryos showing GUS gene expression in less than 5% of their scutellum); and 0 (immature embryos showing no GUS gene expression). In the horizontal axis, "SG" denotes silica gel, "HA" denotes hydroxyapatite, and "GW" denotes ground glass wool. "None" represents a control treated in the absence of any powder.

FIG. 9 is a graph showing the effect of powder addition (mixed into an inoculum) on transient expression of a transgene in immature rice embryos inoculated with a normal binary vector. Eleven to twelve immature embryos were inoculated for each test. The vertical axis represents expression of the GUS gene in the immature embryos. The value is evaluated as follows: co-cultured immature embryos are stained with X-Gluc and then classified into the following levels: 3 (immature embryos showing GUS gene expression in 75% or more of their scutellum); 2 (immature embryos showing GUS gene expression in 25% to 74% of their scutellum); 1 (immature embryos showing GUS gene expression in 5% to 24% of their scutellum); 0.5 (immature embryos showing GUS gene expression in less than 5% of their scutellum); and 0 (immature embryos showing no GUS gene expression). In the horizontal axis, "GW" and "HA" denote ground glass wool and hydroxyapatite, respectively. "None" represents a control treated in the absence of any powder.

EXAMPLES

The present invention will now be further described in the following examples, which are not intended to limit the technical scope of the invention. Based on the detailed description, modifications and changes will be apparent to those skilled in the art, and such modifications and changes fall within the technical scope of the invention.

Example 1

Transformation of Rice in the Presence of Powder

Material and Method (1) Strain and Plasmid of *Agrobacterium*

LBA4404(pSB134) was used as an *Agrobacterium* strain and its vector. LBA4404(pSB134) was created as follows. A GUS expression unit derived from pIG221 (Ohta, S., et al., (1990) Plant Cell Physiol., 31: 805-813) was inserted at a HindIII restriction site located upstream of the HPT gene under the control of the maize ubiquitin promoter in pKY205 (Kuraya, Y., et al., (2004) Mol. Breed., 14: 309-320). This plasmid was introduced into LBA4404(pSB1) (Komari, T., et al., (1996) Plant J., 10: 165-174) to obtain LBA4404 (pSB134).

(2) Test Cultivar and Tissue

The test cultivar used was a japonica rice cultivar "Yukihikari." Immature seeds at 8 to 14 days after flowering were treated to remove their glumes and sterilized with 70% ethanol for several seconds and then with a 1% aqueous sodium hypochlorite solution containing Tween 20 (Wako Pure Chemical Industries, Ltd., Japan) for 15 minutes. After washing several times with sterilized water, immature embryos of 1.5-2 mm in length were excised for use as test materials.

(3) Inoculum Preparation

The powders used for testing were hydroxyapatite (Bio-Rad) and silica gel (ICN Pharmaceuticals). These powders (80 to 100 mg each) were introduced into tubes and sterilized in an autoclave. *Agrobacterium* colonies cultured on AB medium (Chilton, M-D, et al., (1974) Proc. Natl. Acad. Sci. USA, 71: 3672-3676) for 3 to 5 days were collected by scraping with a platinum loop and suspended at a concentration of $1 \times 10^8$ to $1 \times 10^9$ cfu/ml in modified AA medium (AA major inorganic salts, AA amino acids and AA vitamins (Toriyama K., et al., (1985) Plant Sci., 41: 179-183), MS minor salts (Murashige, T. and Skoog, F., (1962) Physiol. Plant, 15: 473-497), 1.0 g/l casamino acid, 100 μM acetosyringone, 0.2 M sucrose, 0.2 M glucose). The resulting *Agrobacterium* suspension (1 ml) was added to each powder-containing tube for use as an inoculum.

(4) Inoculation and Co-Culture

The aseptically excised immature embryos were plated onto 2N6-AS medium. After mixing with a vortex mixer for several seconds to ensure a uniformly dispersed state of the powder in the bacterial suspension, the suspension was added dropwise onto the immature embryos in a volume of 5 μl per immature embryo. After the inoculum added dropwise was dried, the immature embryos were each transferred to another site on the same medium. After the culture container was sealed, co-culture was performed at 25° C. in the dark for 7 days. Some of the immature embryos were treated with X-Gluc to examine GUS expression (Hiei et al., 1994). Namely, immediately after co-culture, each tissue was immersed in 0.1 M phosphate buffer (pH 6.8) containing 0.1% Triton X-100 and allowed to stand at 37° C. for 1 hour. *Agrobacterium* was removed with phosphate buffer, followed by addition of phosphate buffer containing 1.0 mM 5-bromo-4-chloro-3-indolyl-β-D-glucuronic acid (X-Gluc) and 20% methanol. After incubation at 37° C. for 24 hours, tissues showing blue staining were observed under a microscope.

(5) Selection and Regeneration

The co-cultured immature embryos were each divided into 4 to 6 parts with a scalpel and plated onto nN6CC medium (N6 inorganic salts, N6 vitamins, 0.5 g/l casamino acid, 0.5 g/l L-proline, 1 mg/l 2,4-D, 0.5 mg/l NAA, 0.1 mg/l 6BA, 20 g/l sucrose, 55 g/l sorbitol, 250 mg/l cefotaxime, 250 mg/l carbenicillin, 5 g/l Gelrite, pH 5.8) or NBK4CC (NBK4 major inorganic salts, B5 minor inorganic salts, B5 vitamins, AA amino acids, 0.5 g/l casamino acid, 0.5 g/l L-proline, 1 mg/l 2,4-D, 0.5 mg/l NAA, 0.1 mg/l 6BA, 20 g/l maltose, 55 g/l sorbitol, 250 mg/l cefotaxime, 250 mg/l carbenicillin, 5 g/l Gelrite, pH 5.8). After culture in the light at 28° C. for 1 week, the resulting calli were each divided into 5 parts, plated onto 50 mg/l hygromycin-containing nN6CC or NBK4CC medium, and then cultured for 10 days under the same conditions. The proliferated cell clumps were plated onto a 50 mg/l hygromycin-containing regeneration medium (N6 inorganic salts, N6 vitamins, AA amino acids, 1 g/l casamino acid, 0.5 mg/l kinetin, 20 g/l sucrose, 30 g/l sorbitol, 4 g/l Gelrite, pH 5.8) or (NBK4 major inorganic salts, B5 minor inorganic salts, B5 vitamins, AA amino acids, 1 g/l casamino acid, 2 mg/l kinetin, 20 g/l maltose, 30 g/l sorbitol, 5 g/l Gelrite, pH 5.8), and then cultured for about 2 weeks under the same conditions.

(6) Calculation of Transformation Efficiency

In immature rice embryos inoculated with *Agrobacterium*, spots indicative of transient expression of the GUS gene are observed over a wide area of the scutellum. Spots observed at separate sites even on the same scutellum are recognized to be derived from different transformed cells individually gene-transferred. In a case where immature embryos proliferated after co-culture and resting culture are each divided into 4 to 6 blocks and the resulting 20 to 30 cell clumps are proliferated in the presence of hygromycin, calli proliferated therefrom and their regenerated plants are regarded as independent transformants even if they are derived from a single immature embryo.

With respect to hygromycin-resistant calli proliferated from cell clumps obtained by embryo division, one callus was selected from one cell clump and plated onto a hygromycin-containing regeneration medium. Among regenerated plants obtained therefrom, those showing hygromycin resistance were counted as transformants, and the total number was divided by the number of inoculated immature embryos to calculate the transformation efficiency.

Results (7) Transient Expression of Transgene

The co-cultured immature embryos were treated with X-Gluc. Although blue spots indicative of transient expression of the GUS gene were observed in immature embryos in each case, the immature embryos inoculated with the powder-containing inoculums had a wider area of blue staining than the control immature embryos treated in the absence of any powder. This indicated that powder addition promoted gene transfer.

(8) Transformation Efficiency

Figure 1:
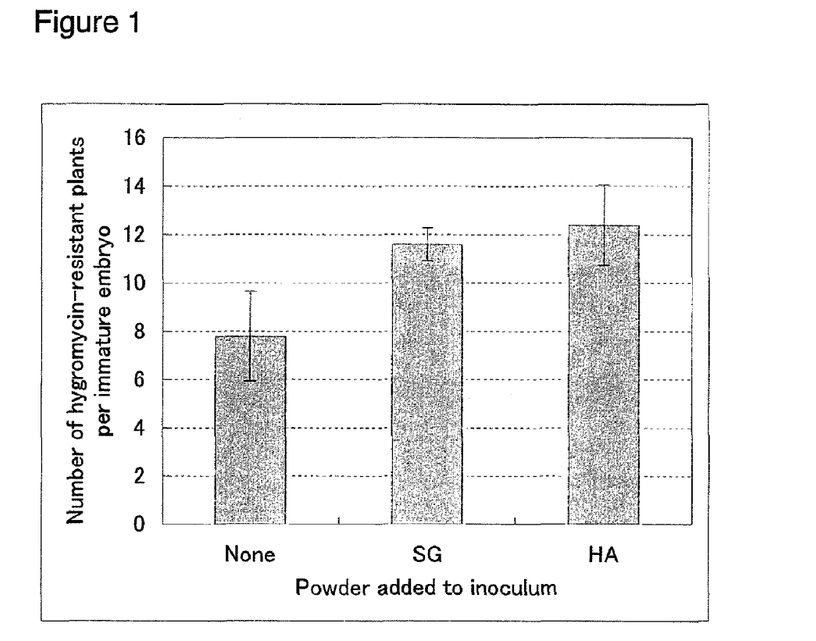
FIG. 1 is a graph showing the effect of powder addition on transformation efficiency in rice. Five immature embryos were inoculated for each test. The vertical axis represents the number of hygromycin-resistant plants obtained per inoculated immature embryo, while "SG" and "HA" in the horizontal axis denote silica gel and hydroxyapatite, respectively.

The co-cultured immature embryos were cultured on a hygromycin-containing medium, and the resulting calli were plated and cultured on a hygromycin-containing regeneration medium. Although hygromycin-resistant regenerated plants were obtained from immature embryos in each case, the immature embryos inoculated with the powder-containing inoculums resulted in a larger number of hygromycin-resistant regenerated plants than the control immature embryos treated in the absence of any powder. This indicated that powder addition improved the transformation efficiency (FIG. 1).

Example 2

Transformation of Maize in the Presence of Powder

Material and Method (1) Strain and Plasmid of *Agrobacterium*

LBA4404(pSB131) (Ishida, Y., et al., (1996) Nature Biotechnology, 14: 745-750) was used as an *Agrobacterium* strain and its vector.

(2) Test Cultivar and Tissue

The test cultivar used was a maize inbred line A188. From kernels at 8 to 14 days after crossing, immature embryos of 1.0-1.2 mm in size were aseptically excised for use as test materials.

(3) Inoculum Preparation

The powders used for testing were hydroxyapatite (Bio-Rad), silica gel (ICN Pharmaceuticals) and mortar-ground glass wool. These powders (80 to 100 mg each) were introduced into tubes and sterilized in an autoclave. *Agrobacterium* colonies cultured on YP medium (5 g/l yeast extract, 10 g/l peptone, 5 g/l NaCl, pH 6.8) for 3 to 5 days were collected by scraping with a platinum loop and suspended at a concentration of $1 \times 10^8$ to $1 \times 10^9$ cfu/ml in LS-inf medium (Ishida, Y., et al., (1996) Nature Biotechnology, 14: 745-750). The resulting *Agrobacterium* suspension (1 ml) was added to each powder-containing tube for use as an inoculum.

(4) Inoculation and Co-Culture

Inoculation was accomplished in two ways, i.e., standard inoculation and drop inoculation.

Standard inoculation was accomplished as follows. The aseptically excised immature embryos were treated at 46° C. for 3 minutes and then centrifuged at 15,000 rpm at 4° C. for 10 minutes. The heat-treated and centrifuged immature embryos were mixed with the inoculum and mixed with a vortex mixer for 30 seconds. The immature embryos were plated onto LS-AS medium containing 5 µM $AgNO_3$ and 5 µM $CuSO_4$. After the culture container was sealed, co-culture was performed at 25° C. in the dark for 7 days.

Drop inoculation was accomplished as follows. The heat-treated and centrifuged immature embryos were plated onto LS-AS medium containing 5 µl $AgNO_3$ and 5 mM $CuSO_4$. After lightly mixing with a vortex mixer to ensure a uniformly dispersed state of the powder in the bacterial suspension, the suspension was added dropwise onto the immature embryos in a volume of 5 µl per immature embryo. After the inoculum added dropwise was dried, the immature embryos were each transferred to another site on the same medium. After the culture container was sealed, co-culture was performed at 25° C. in the dark for 7 days.

Some of the immature embryos were treated with X-Gluc to examine GUS expression (Hiei, Y., et al., (1994) The Plant Journal, 6: 271-282). Namely, immediately after co-culture, each tissue was immersed in 0.1 M phosphate buffer (pH 6.8) containing 0.1% Triton X-100 and allowed to stand at 37° C. for 1 hour. *Agrobacterium* was removed with phosphate buffer, followed by addition of phosphate buffer containing 1.0 mM 5-bromo-4-chloro-3-indolyl-β-D-glucuronic acid (X-Gluc) and 20% methanol. After incubation at 37° C. for 24 hours, tissues showing blue staining were observed under a microscope.

(5) Selection and Regeneration

The immature embryos were plated onto modified LSD1.5 medium (Ishida, Y., et al., (2003) Plant Biotechnology, 20: 57-66) containing 5 mg/l phosphinothricin (PPT) and cultured in the dark at 25° C. for 10 to 14 days, followed by culture on modified LSD1.5 medium containing 10 mg/l PPT. The proliferated cell clumps were plated onto LSZ regeneration medium (Ishida, Y., et al., (1996) Nature Biotechnology, 14: 745-750) containing 5 mg/l PPT and 10 µM $CuSO_4$, and then cultured in the light at 25° C. for about 2 weeks. Leaves of the regenerated plants were partially excised and treated with X-Gluc to examine GUS expression.

Results (6) Transient Expression of Transgene

The co-cultured immature embryos were treated with X-Gluc. Although blue spots indicative of transient expression of the GUS gene were observed in immature embryos in each case, the immature embryos inoculated with the powder-containing inoculums had a wider area of blue staining than the control immature embryos treated in the absence of any powder, in both cases of standard inoculation and drop inoculation. This indicated that powder addition promoted gene transfer.

(7) Transformation Efficiency

The co-cultured immature embryos were cultured on a PPT-containing medium, and the resulting calli were plated and cultured on a PPT-containing regeneration medium. GUS analysis was performed on regenerated PPT-resistant plants. Although GUS-positive plants were obtained from immature embryos in each case, the immature embryos inoculated with the powder-containing inoculums resulted in a larger number of GUS-positive plants than the control immature embryos treated in the absence of any powder, in both cases of standard inoculation and drop inoculation. This indicated that powder addition improved the transformation efficiency (Table 1). Powder addition-induced improvement in the transformation efficiency was observed not only in the case where immature embryos were mixed in the presence of *Agrobacterium* and the powder and then plated onto the co-culture medium (standard inoculation), but also in the case where a mixture of the powder and *Agrobacterium* was added dropwise onto immature embryos (drop inoculation). This indicates that improvement of the transformation efficiency does not result from powder-induced injury in plant tissue.

TABLE 1

Effect of powder addition on maize transformation efficiency

| Inoculation | Powder | Number of immature embryos Inoculated | Regenerated | Regenerated (%) | GUS-positive | GUS-positive (%) |
| --- | --- | --- | --- | --- | --- | --- |
| Standard inoculation | None | 31 | 11 | 35.5 | 4 | 12.9 |
|  | GW | 32 | 13 | 40.6 | 7 | 21.9 |
|  | SG | 28 | 12 | 42.9 | 5 | 17.9 |
|  | HA | 27 | 13 | 48.1 | 5 | 18.5 |

TABLE 1-continued

Effect of powder addition on maize transformation efficiency

| Inoculation | Powder | Number of immature embryos Inoculated | Regenerated | Regenerated (%) | GUS-positive | GUS-positive (%) |
|---|---|---|---|---|---|---|
| Drop inoculation | None | 13 | 6 | 46.2 | 1 | 7.7 |
| | GW | 13 | 7 | 53.8 | 4 | 30.8 |
| | SG | 12 | 9 | 75.0 | 2 | 16.7 |
| | HA | 12 | 5 | 41.7 | 2 | 16.7 |

GW, ground glass wool; SG, silica gel; HA, hydroxyapatite

Example 3

Effect of Powder Particle Size (Silica Gel)

Material and Method (1) Strain and Plasmid of *Agrobacterium*

LBA4404(pSB134) was used as an *Agrobacterium* strain and its vector.

(2) Test Cultivar and Tissue

The test cultivar used was a japonica rice cultivar "Yukihikari." Immature seeds at 8 to 14 days after flowering were treated to remove their glumes and sterilized with 70% ethanol for several seconds and then with a 1% aqueous sodium hypochlorite solution containing Tween 20 for 15 minutes. After washing several times with sterilized water, immature embryos of 1.5-2 mm in length were excised for use as test materials.

(3) Inoculum Preparation

The powders used for testing were 5 types of silica gel having different particle sizes (particle size: 5-20 μm, 20-40 μm, 45-75 μm, 75-150 μm and 150-425 μm; Wako Pure Chemical Industries, Ltd., Japan). These powders (120 mg each) were introduced into tubes and sterilized in an autoclave. *Agrobacterium* colonies cultured on AB medium (Chilton, M-D., et al., (1974) Proc. Natl. Acad. Sci. USA, 71: 3672-3676) for 3 to 5 days were collected by scraping with a platinum loop and suspended at a concentration of $1\times10^8$ to $1\times10^9$ cfu/ml in modified AA medium (AA major inorganic salts, AA amino acids and AA vitamins (Toriyama, K., et al., (1985) Plant Sci., 41: 179-183), MS minor salts (Murashige, T. and Skoog, F., (1962) Physiol. Plant, 15: 473-497), 1.0 g/l casamino acid, 100 KM acetosyringone, 0.2 M sucrose, 0.2 M glucose). The resulting *Agrobacterium* suspension (1 ml) was added to each powder-containing tube for use as an inoculum.

(4) Production of Transformed Plant

Inoculation, co-culture, selection, regeneration, and calculation of the transformation efficiency were performed as described in Example 1.

Results (5) Transient Expression of Transgene

The co-cultured immature embryos were treated with X-Gluc. Although blue spots indicative of transient expression of the GUS gene were observed in all cases (including the control treated in the absence of any powder), the immature embryos inoculated with the inoculums containing silica gel having a particle size of 150 μm or less had a wider area of blue staining than the control treated in the absence of any powder and the immature embryos inoculated with the inoculum containing 150 μm or more powder. This indicated that the degree of promoting gene transfer would vary depending on the particle size of a powder.

(6) Transformation Efficiency

Figure 2:
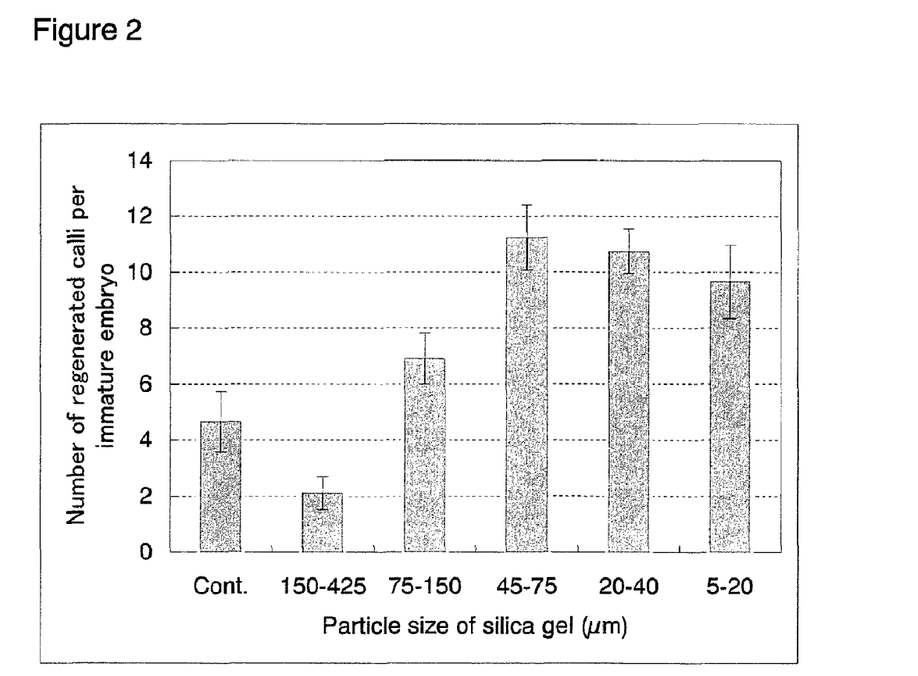
FIG. 2 is a graph showing the effect of powder particle size on transformation efficiency in rice. Nine to twelve immature embryos were inoculated for each test. The vertical axis represents the number of regenerated calli obtained per inoculated immature embryo, while the horizontal axis represents the particle size of each powder added. "Cont." denotes a control treated in the absence of any powder.

The co-cultured immature embryos were cultured on a hygromycin-containing medium, and the resulting calli were plated and cultured on a hygromycin-containing regeneration medium. Although hygromycin-resistant regenerated plants were obtained from immature embryos in each case, the immature embryos inoculated with the inoculums containing silica gel having a particle size of 150 μm or less resulted in a larger number of hygromycin-resistant regenerated plants than the control immature embryos treated in the absence of any powder, and hence showed improved transformation efficiency (FIG. 2).

Example 4

Effect of Powder Amount (Activated Charcoal and Silica Gel)

Material and Method (1) Strain and Plasmid of *Agrobacterium*

LBA4404(pSB134) was used as an *Agrobacterium* strain and its vector.

(2) Test Cultivar and Tissue

The test cultivar used was a japonica rice cultivar "Yukihikari." Immature seeds at 8 to 14 days after flowering were treated to remove their glumes and sterilized with 70% ethanol for several seconds and then with a 1% aqueous sodium hypochlorite solution containing Tween 20 for 15 minutes. After washing several times with sterilized water, immature embryos of 1.5-2 mm in length were excised for use as test materials.

(3) Inoculum Preparation

The powders used for testing were activated charcoal and silica gel (Wako Pure Chemical Industries, Ltd., Japan). These powders (0 to 240 mg each) were introduced into tubes and sterilized in an autoclave. *Agrobacterium* colonies cultured on AB medium (Chilton, M-D., et al., (1974) Proc. Natl. Acad. Sci. USA, 71: 3672-3676) for 3 to 5 days were collected by scraping with a platinum loop and suspended at a concentration of $1\times10^8$ to $1\times10^9$ cfu/ml in modified AA medium (AA major inorganic salts, AA amino acids and AA vitamins (Toriyama, K., et al., (1985) Plant Sci., 41: 179-183), MS minor salts (Murashige, T. and Skoog, F., (1962) Physiol. Plant, 15: 473-497), 1.0 g/l casamino acid, 100 mM acetosyringone, 0.2 M sucrose, 0.2 M glucose). The resulting *Agrobacterium* suspension (1 ml) was added to each powder-containing tube for use as an inoculum.

(4) Inoculation, Co-Culture and Production of Transformed Plant

Inoculation, co-culture, selection, regeneration, and calculation of the transformation efficiency were performed as described in Example 1.

Results (5) Transient Expression of Transgene

Figure 3:
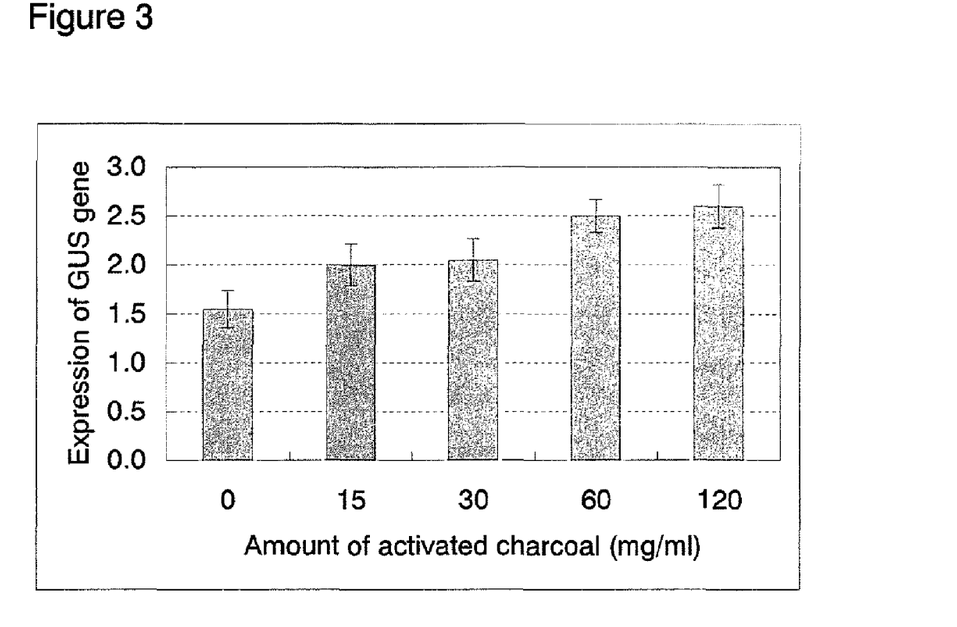

The co-cultured immature embryos were treated with X-Gluc. Although blue spots indicative of transient expression of the GUS gene were observed in all cases (including the control treated in the absence of any powder), the immature embryos inoculated with the inoculums containing activated charcoal in an amount of 60 mg or more per ml inoculum had a wider area of blue staining than the control treated in the absence of any powder and the immature embryos inoculated with the inoculums containing 30 mg or less powder. This indicated that the degree of promoting gene transfer would vary depending on the amount of a powder added to an inoculum (FIG. 3).

(6) Transformation Efficiency

Figure 4:
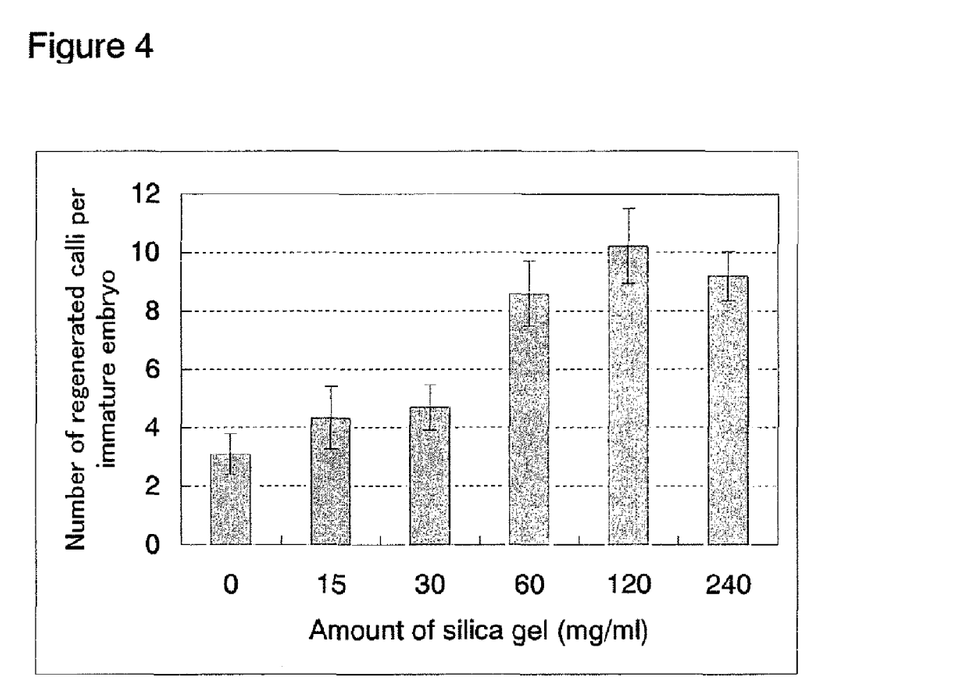
FIG. 4 is a graph showing the effect of powder amount on transformation efficiency in rice. Nine to ten immature embryos were inoculated for each test. The vertical axis represents the number of regenerated calli obtained per inoculated immature embryo, while the horizontal axis represents the powder amount added.

The co-cultured immature embryos were cultured on a hygromycin-containing medium, and the resulting calli were plated and cultured on a hygromycin-containing regeneration medium. Although hygromycin-resistant regenerated plants were obtained from immature embryos in each case, the immature embryos inoculated with the inoculums containing 30 mg or more silica gel resulted in a larger number of hygromycin-resistant regenerated plants than the control immature embryos treated in the absence of any powder, and hence showed improved transformation efficiency (FIG. 4).

Example 5

Effect of Zeolite

Material and Method (1) Strain and Plasmid of *Agrobacterium*

LBA4404(pSB131) was used as an *Agrobacterium* strain and its vector.

(2) Test Cultivar and Tissue

The test cultivar used was a maize inbred line A188. From kernels at 8 to 14 days after crossing, immature embryos of 1.0-1.2 mm in size were aseptically excised for use as test materials.

(3) Inoculum Preparation

The powders used for testing were 2 types of zeolite having different particle sizes (5 μm and 75 μm; Wako Pure Chemical Industries, Ltd., Japan). Powder sterilization and inoculum preparation were performed as described in Example 2.

(4) Inoculation and Co-Culture

Inoculation was accomplished through drop inoculation as described in Example 2. Examination of GUS expression in the co-cultured immature embryos was accomplished as described in Example 2.

Results (5) Transient Expression of Transgene

Figure 5:
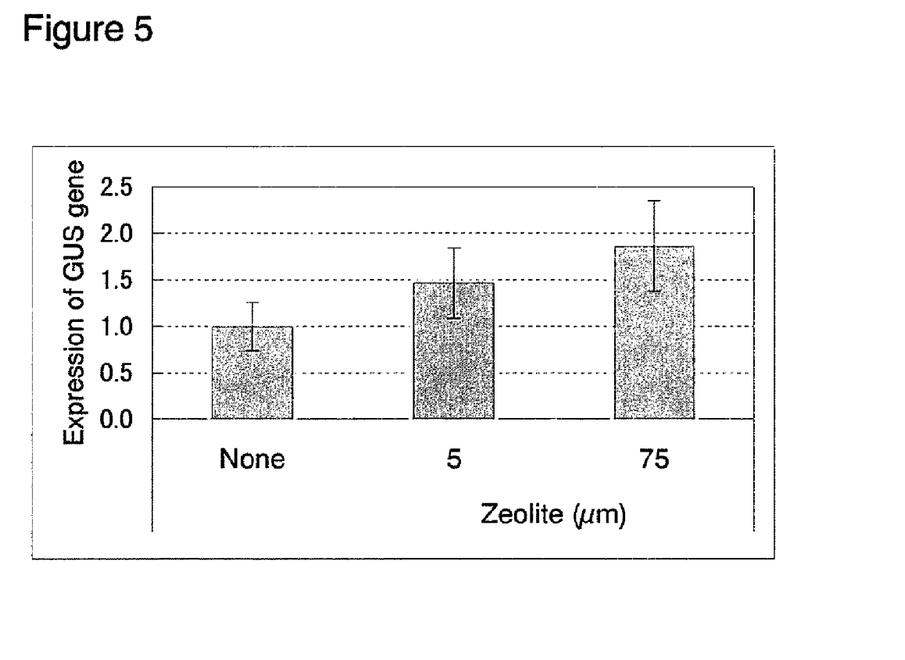

The co-cultured immature embryos were treated with X-Gluc. Although blue spots indicative of transient expression of the GUS gene were observed in immature embryos in each case, the immature embryos inoculated with the inoculums containing zeolite showed a wider area of GUS gene expression than the control immature embryos. When compared to zeolite having a particle size of 5 μm, a much wider area of GUS gene expression was observed in zeolite having a particle size of 75 μm (FIG. 5).

Example 6

Effect of Mixed Powders

Material and Method (1) Strain and Plasmid of *Agrobacterium*

LBA4404(pSB134) was used as an *Agrobacterium* strain and its vector.

(2) Test Cultivar and Tissue

The test cultivar used was a japonica rice cultivar "Yukihikari." Test materials were prepared as described in Example 4.

(3) Inoculum Preparation

The powders used for testing were silica gel, hydroxyapatite and ground glass wool. These powders (120 mg in total) were introduced into tubes and sterilized in an autoclave. In the case of mixing two powders, the powders of about 60 mg each were introduced into a tube and sterilized. Likewise, in the case of mixing three powders, the powders of about 40 mg each were introduced into a tube and sterilized. An *Agrobacterium* suspension was prepared as described in Example 4. The resulting *Agrobacterium* suspension (1 ml) was added to each powder-containing tube for use as an inoculum.

(4) Inoculation and Co-Culture

Inoculation, co-culture, and examination of GUS expression were performed as described in Example 1.

Results (5) Transient Expression of Transgene

Figure 6:
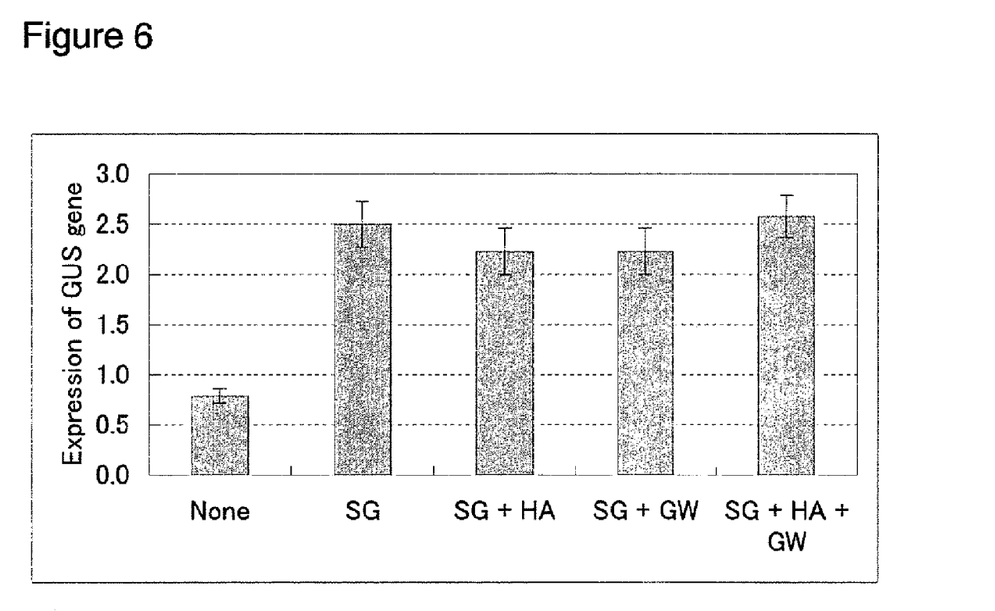

The co-cultured immature embryos were treated with X-Gluc. Although blue spots indicative of transient expression of the GUS gene were observed in all cases (including the control treated in the absence of any powder), the immature embryos inoculated with the powder-containing inoculums had a wider area of blue staining than the control treated in the absence of any powder. There was no great difference in the degree of promoting gene transfer between a single powder and a mixture of 2 or 3 powders (FIG. 6).

Example 7

Transformation of Rice Calli in the Presence of Powder (1) Strain and Plasmid of *Agrobacterium*

LBA4404(pSB134) was used as an *Agrobacterium* strain and its vector.

(2) Test Cultivar and Tissue

The test cultivar used was a japonica rice cultivar "Yukihikari." Immature seeds at 8 to 14 days after flowering were treated to remove their glumes and sterilized with 70% ethanol for several seconds and then with a 1% aqueous sodium hypochlorite solution containing Tween 20 for 15 minutes. After washing several times with sterilized water, immature embryos of 1.5-2 mm in length were excised and plated onto 2N6-AS medium. After culture in the dark at 25° C. for 1 week, immature embryos from which calli were proliferated were used as test materials.

(3) Inoculum Preparation

The powder used for testing was hydroxyapatite (Bio-Rad).

An inoculum was prepared as described in Example 1.

(4) Inoculation and Co-Culture

To confirm transient expression of the transgene, the calli were plated onto 2N6-AS medium. After shaking with a vortex mixer to ensure a uniformly dispersed state of the powder in the bacterial suspension, the suspension was added dropwise onto the calli in a volume of 10 μl per callus. After the inoculum added dropwise was dried, the calli were each transferred to another site on the same medium. Co-culture and examination of GUS expression were performed as described in Example 4.

Production of Transformed Plant

To confirm the transformation efficiency, inoculation, co-culture, selection, regeneration, and calculation of the transformation efficiency were performed on the calli, as described in Example 1. The volume of the bacterial suspension added dropwise was set to 10 μl.

Results (5) Transient Expression of Transgene

Figure 7:
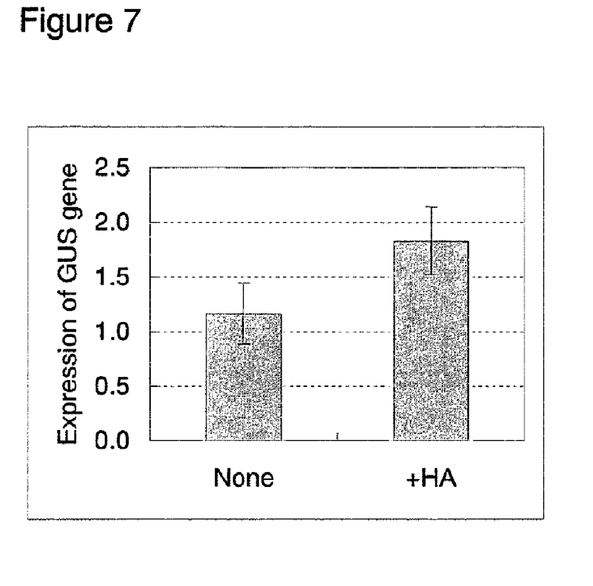
FIG. 7 is a graph showing the effect of powder addition to an inoculum on transient expression of a transgene in rice calli. Six calli were inoculated for each test. The vertical axis represents expression of GUS gene in the inoculated calli. The value is evaluated as follow: co-cultured calli are stained with X-Gluc and then classified into the following levels: 3 (calli showing GUS gene expression in 75% or more of all sites); 2 (calli showing GUS gene expression in 25% to 74% of all sites); 1 (calli showing GUS gene expression in 5% to 24% of all sites); 0.5 (calli showing GUS gene expression in less than 5% of all sites); and 0 (calli showing no GUS gene expression). In the horizontal axis, "HA" denotes hydroxyapatite, and "None" represents a control treated in the absence of any powder.

The co-cultured immature embryos were treated with X-Gluc. The calli inoculated with the hydroxyapatite-containing inoculum had a wider area of blue staining than the calli inoculated with a powder-free inoculum. This indicated that powder addition to an inoculum also promoted gene transfer even when callus was used as a material (FIG. 7).

(6) Transformation Efficiency

Figure 8:
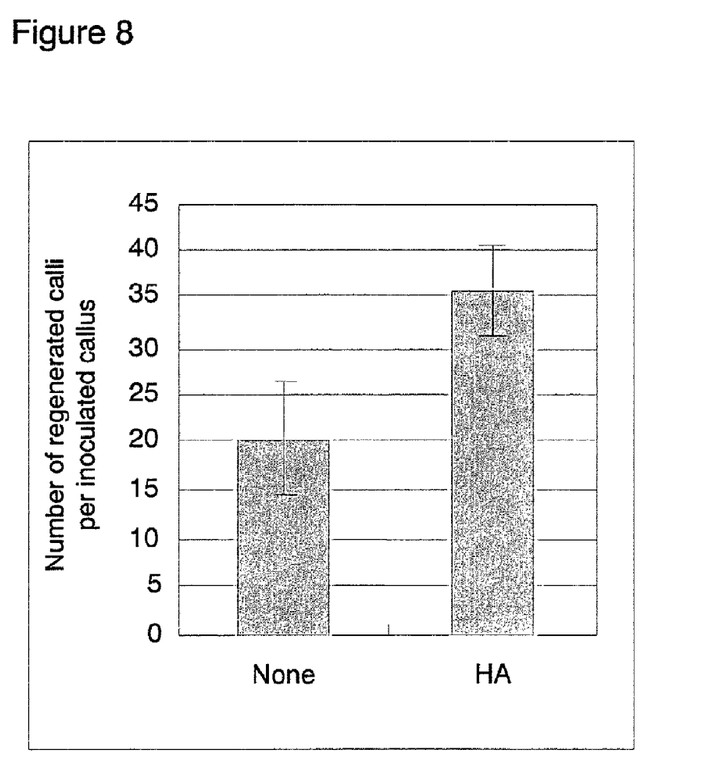
FIG. 8 is a graph showing the effect of powder addition to an inoculum on transformation efficiency in rice. Six calli were inoculated for each test. The vertical axis represents the number of regenerated calli obtained per inoculated callus. In the horizontal axis, "HA" denotes hydroxyapatite, and "None" represents a control treated in the absence of any powder.

The co-cultured calli were cultured on a hygromycin-containing medium, and the proliferated calli were then plated and cultured on a hygromycin-containing regeneration medium. When compared to the calli inoculated with a powder-free inoculum, the calli inoculated with the hydroxyapatite-containing inoculum allowed regeneration of a larger number of hygromycin-resistant plants, and hence showed improved transformation efficiency (FIG. 8).

Example 8

Transformation with Normal Binary Vector in the Presence of Powder (1) Strain and Plasmid of *Agrobacterium*

LBA4404(pIG121Hm) (Hiei, et al., 1994, The Plant Journal, 6: 271-282) was used as an *Agrobacterium* strain and its vector. LBA4404(pIG121Hm) is a normal binary vector which is free from a part of the super-virulent vir gene found in the super-binary vector.

(2) Test Cultivar and Tissue

The test cultivar used was a japonica rice cultivar "Yukihikari." Test materials were prepared as described in Example 4.

(3) Inoculum Preparation

The powders used for testing were ground glass wool and hydroxyapatite. Inoculums were prepared as described in Example 1.

(4) Inoculation and Co-Culture

Inoculation, co-culture, and examination of GUS expression were performed as described in Example 4.

Results (5) Transient Expression of Transgene

Figure 9:
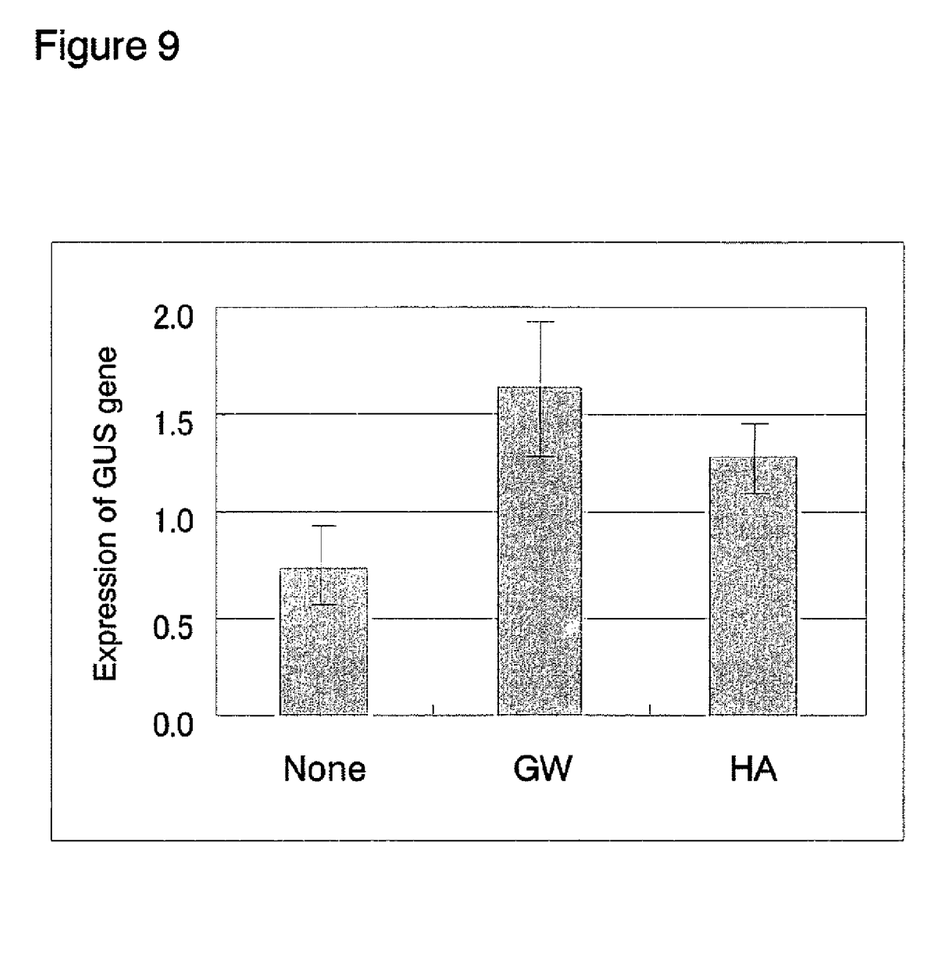

The co-cultured immature embryos were treated with X-Gluc. Although blue spots indicative of transient expression of the GUS gene were observed in all cases (including the control treated in the absence of any powder), the immature embryos inoculated with the inoculum containing ground glass wool or hydroxyapatite had a wider area of blue staining than the immature embryos treated in the absence of any powder. This indicated that powder addition to an inoculum also promoted gene transfer even when a normal binary vector was inoculated (FIG. 9).

Example 9

Southern Analysis

According to the method of Komari et al. (Komari, et al., 1989; Theor. Appl. Genet., 77: 547-552), DNAs were extracted from the transformed plants obtained in Example 1 and additional transformed plants obtained in the same manner as shown in Example 1 by using an inoculum containing ground glass wool or activated charcoal. The extracted DNAs were each treated with a restriction enzyme XbaI and subjected to Southern analysis using the GUS gene as a probe to detect the transgene. Southern analysis was performed as described in Molecular Cloning (Sambrook, et al., 1989; Cold Spring Harbor Laboratory Press). As a result, hybridizing bands were detected at different sites, thus proving that the transgene was randomly inserted in the rice genome. The copy number of the transgene was found to be 1 to 4 (Table 2).

TABLE 2

Copy number of transgene in rice transformants of T0 generation (Southern analysis)

| | Number of transformants | | | |
|---|---|---|---|---|
| | 1 copy | 2 copies | 3 copies | 4 copies |
| None | 4 | 2 | 0 | 0 |
| HA | 2 | 1 | 1 | 2 |
| SG | 2 | 4 | 0 | 0 |
| GW | 3 | 1 | 2 | 0 |
| AC | 5 | 0 | 0 | 1 |

In each case, 6 independent transformed plants were analyzed.
"None" represents a control treated in the absence of any powder, "HA" denotes hydroxyapatite, "SG" denotes silica gel, "GW" denotes ground glass wool, and "AC" denotes activated charcoal.

Example 10

Inheritance of Transgene to Progeny

The transformed plants obtained in Example 1 and additional transformed plants obtained in the same manner as shown in Example 1 by using an inoculum containing ground glass wool were self-fertilized, and the resulting T1 seeds were seeded. Leaves were partially excised from young seedlings at 10 days after seeding to examine expression of the GUS gene, as described in Example 1.

The results obtained are shown in Table 3. Upon statistical analysis (chi-square test) of these results, expression of the GUS gene in T1 plants conformed to a GUS-positive:negative ratio of 3:1 or 15:1 in all cases, thus indicating that the transgene was inherited to progeny according to the Mendel's laws.

TABLE 3

Expression of transgene in T1 generation progeny of rice transformants

| | Number of T1 generation progeny | |
|---|---|---|
| Transformant | GUS-positive | GUS-negative |
| None | 11 | 2 |
| HA1 | 15 | 1 |
| HA2 | 10 | 2 |
| HA3 | 6 | 3 |
| SG1 | 14 | 2 |
| SG2 | 14 | 1 |
| SG3 | 9 | 1 |
| GW1 | 5 | 1 |
| GW2 | 6 | 2 |
| Non-transformed | 0 | 13 |

"None" represents a control treated in the absence of any powder, "HA" denotes hydroxyapatite, "SG" denotes silica gel, and "GW" denotes ground glass wool. "Non-transformed" denotes a non-transformed cultivar Yukihikari.

Industrial Applicability

The present invention provides a convenient method for gene transfer and transformation with higher efficiency than that achieved by conventional *Agrobacterium*-mediated methods. The present invention improved the efficiency of *Agrobacterium*-mediated gene transfer and transformation in plants, thereby allowing many transformed plants to be efficiently obtained, and contributing to efficient growth of cultivars containing a practical gene.

The invention claimed is:

1. A method for producing a transformed plant through *Agrobacterium*-mediated transformation in a plant material, which comprises the following steps:

(1) inoculating an *Agrobacterium* suspension into the plant material in the presence of a powder, wherein said powder has a particle size of 1 to 150 μm;
(2) selecting a transformed plant material; and
(3) regenerating the selected transformant;
wherein said plant is a Gramineae plant, and wherein said plant material is an immature embryo or a callus.

2. The method according to claim 1, wherein the powder is selected from the group consisting of hydroxyapatite, silica gel, zeolite glass wool, activated charcoal, and mixtures thereof.

3. The method according to claim 1, wherein the powder has a particle size of 5 to 75 μm.

4. The method according to claim 1, wherein the Gramineae plant is selected from the group consisting of rice, maize, barley, wheat and sorghum.

5. The method according to claim 1, wherein step (1) is accomplished by:
(i) mixing the *Agrobacterium* suspension with the powder; and
(ii) inoculating the mixture from (i) into the plant material.

6. The method according to claim 1, wherein step (1) is accomplished by:
(i) mixing the plant material with the powder; and
(ii) inoculating the mixture from (i) with the *Agrobacterium* suspension.

7. The method according to claim 1, wherein step (1) is accomplished by mixing together the *Agrobacterium* suspension, the powder and the plant material to thereby inoculate the *Agrobacterium* into the plant material.

8. The method according to claim 1, wherein said inoculating step is conducted by drop inoculation.

9. The method according to claim 5, wherein said inoculating step is conducted by drop inoculation.

* * * * *